United States Patent
Kimura (10) Patent No.: US 8,840,568 B2
(45) Date of Patent: Sep. 23, 2014

(54) DEVICE FOR THE MEDICAL TREATMENT

(75) Inventor: Ayako Kimura, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 15 days.

(21) Appl. No.: 13/356,715

(22) Filed: Jan. 24, 2012

(65) Prior Publication Data

US 2012/0253318 A1    Oct. 4, 2012

(30) Foreign Application Priority Data

Mar. 28, 2011   (JP) ................. 2011-070991

(51) Int. Cl.
  *A61B 5/00*   (2006.01)
  *A61M 25/09*  (2006.01)

(52) U.S. Cl.
  CPC .............. *A61M 25/09041* (2013.01)
  USPC ... 600/585; 600/434; 604/164.1; 604/164.13; 604/533; 606/194; 206/364

(58) Field of Classification Search
  USPC .......... 600/434, 585; 604/164.1, 164.13, 533; 606/194; 206/364
  See application file for complete search history.

(56) References Cited

U.S. PATENT DOCUMENTS

| | | | | |
|---|---|---|---|---|
| 4,957,117 A * | 9/1990 | Wysham ................. | 600/585 |
| 5,137,517 A * | 8/1992 | Loney et al. ............ | 604/159 |
| 5,191,888 A * | 3/1993 | Palmer et al. .......... | 600/434 |
| 5,234,002 A * | 8/1993 | Chan ....................... | 600/585 |
| 5,361,777 A * | 11/1994 | Sellers .................... | 600/585 |
| 5,415,177 A * | 5/1995 | Zadini et al. ........... | 600/585 |
| 5,423,331 A * | 6/1995 | Wysham ................. | 600/585 |
| 5,465,733 A * | 11/1995 | Hinohara et al. ....... | 600/585 |
| 5,755,695 A * | 5/1998 | Erickson et al. ........ | 604/164.13 |
| 6,071,287 A * | 6/2000 | Verbeek .................. | 623/1.11 |
| 6,187,016 B1 * | 2/2001 | Hedges et al. .......... | 606/108 |
| 6,197,001 B1 * | 3/2001 | Wilson et al. .......... | 604/157 |
| 6,714,809 B2 * | 3/2004 | Lee et al. ................ | 600/423 |
| 6,796,948 B2 * | 9/2004 | Kanesaka ................ | 600/585 |
| 7,331,966 B2 | 2/2008 | Soma et al. | |
| 7,951,092 B2 * | 5/2011 | Jones et al. ............. | 600/585 |
| 8,038,628 B2 * | 10/2011 | von Malmborg et al. | 600/585 |
| 8,267,873 B2 * | 9/2012 | Yanuma ................... | 600/585 |
| 2002/0161421 A1 * | 10/2002 | Lee et al. ................. | 607/116 |
| 2003/0158561 A1 * | 8/2003 | Kanesaka ................ | 606/108 |
| 2004/0039306 A1 * | 2/2004 | Eberhart et al. ........ | 600/585 |
| 2005/0148820 A1 * | 7/2005 | Carrillo .................. | 600/154 |
| 2006/0009783 A1 * | 1/2006 | Rome et al. ............. | 606/108 |

(Continued)

FOREIGN PATENT DOCUMENTS

| | | |
|---|---|---|
| JP | H06-017751 U | 3/1994 |
| JP | H09-173465 A | 7/1997 |
| JP | 2009-189386 A | 8/2009 |
| JP | 4653958 B2 | 3/2011 |

*Primary Examiner* — Scott Medway (74) *Attorney, Agent, or Firm* — Fitch, Even, Tabin & Flannery LLP (57) ABSTRACT

A device for the medical treatment is provided which includes not only a function for applying turning force to a guide wire but also a function for inserting an end portion of the guide wire into an opening of a catheter and therefore is excellent in workability. In one form, a device for the medical treatment includes a guide wire connecting section capable of being connected to a guide wire to apply turning force to the guide wire, and a catheter connecting section to which a catheter can be connected and which can relatively move toward and away from the guide wire connecting section.

7 Claims, 10 Drawing Sheets

(56) References Cited

U.S. PATENT DOCUMENTS

| | | |
|---|---|---|
| 2007/0219467 A1* | 9/2007 | Clark et al. .................. 600/585 |
| 2007/0270755 A1* | 11/2007 | Von Oepen et al. ..... 604/164.13 |
| 2009/0105653 A1* | 4/2009 | Spenser et al. ........... 604/164.13 |
| 2010/0056910 A1* | 3/2010 | Yanuma ........................ 600/434 |
| 2012/0210569 A1* | 8/2012 | Schmitt ........................... 29/700 |

* cited by examiner

DEVICE FOR THE MEDICAL TREATMENT

CROSS-REFERENCE TO RELATED APPLICATION

This application claims priority under 35 U.S.C. §119 to Japanese Patent Application No. JP2011-070991 filed on Mar. 28, 2011, the entire content of which is hereby incorporated herein by reference in its entirety.

FIELD OF THE INVENTION

The present invention relates to a device for the medical treatment which applies turning force to a guide wire and another device for the medical treatment which inserts an end portion of a guide wire into an opening of a catheter.

BACKGROUND OF THE INVENTION

Conventionally, a catheter is used to carry out a medical treatment and so forth in an organism through a blood vessel, and a guide wire is used to guide a catheter introduced in a blood vessel to a target position. Normally, the guide wire is inserted into a blood vessel through a sheath endermically introduced in the blood vessel and is pushed to advance to the target position while a turning operation or a back and forth operation is carried out on the outside of the organism. To this end portion, a method is known that, in order to facilitate a turning operation and a back and forth operation of the guide wire, a turning force applying tool (torque device) for being grasped with fingers by the operator is connected to an end portion of the guide wire on the outside of the organism (for example, refer to Japanese Patent Laid-Open No. Hei 9-173465).

Then, if the guide wire reaches the target position, then an end portion of the guide wire on the outside of the organism can be inserted into an opening of the catheter on the distal end side to push the catheter to advance to the target position along the guide wire. Then, where a turning force applying tool is connected to an end portion of the guide wire, although the guide wire is inserted into the opening of the catheter after the turning force applying tool is removed, since the opening of the catheter is very small, the insertion operation is not easy. Therefore, an introduction assisting tool (inserter) for inserting an end portion of a guide wire into an opening of a catheter is known (for example, refer to Japanese Patent Document Laid-Open No. 2009-189386). The introduction assisting tool disclosed in Japanese Patent Laid-Open No. 2009-189386 has a structure that a distal end portion of a catheter is fixed to a groove and a guide wire is inserted from a funnel-shaped introduction portion whose diameter gradually decreases from a wide introduction port so that the guide wire is guided to the small diameter opening of the catheter.

SUMMARY OF THE INVENTION

However, where a guide wire is inserted into an opening of a catheter using an introduction assisting tool after a turning force applying tool is removed from the guide wire, the insertion work is complicated and the workability is not good.

The present invention has been made to solve the subject described above, and it is an object of the present invention to provide a device for the medical treatment which includes not only a function for applying turning force to a guide wire but also a function for inserting an end portion of the guide wire into an opening of a catheter and is excellent in workability.

A device for the medical treatment of the present invention which achieves the object described above is a device for the medical treatment including a guide wire connecting section capable of being connected to a guide wire to apply turning force to the guide wire, and a catheter connecting section to which a catheter can be connected and which can relatively move toward and away from the guide wire connecting section.

With the device for the medical treatment according to the present invention, since the guide wire connecting section capable of being connected to a guide wire to apply turning force to the guide wire is provided, it can apply turning force to the guide wire to operate the guide wire. Further, since the present device for the medical treatment includes the catheter connecting section which can relatively move toward and away from the guide wire connecting section with a catheter connected thereto, it is possible to move the guide wire fixed to the guide wire connecting section toward the catheter connected to the catheter connecting section thereby to easily insert the guide wire into the opening of the catheter. Consequently, the device for the medical treatment is superior in workability.

If the device for the medical treatment is configured such that the guide wire connecting section has a grasping section which can move toward and away from the guide wire to grasp or release the guide wire and which releases the guide wire by the movement of the guide wire connecting section and the catheter connecting section toward each other, then the guide wire can be released in an interlocked relationship with the movement of the guide wire connecting section and the catheter connecting section toward each other, resulting in improvement in workability.

If the guide wire connecting section may have a guide wire accommodation groove which extends from the grasping section and can accommodate the guide wire therein, the catheter connecting section having a catheter accommodation groove which can accommodate and hold the catheter therein and extends coaxially with the guide wire accommodation groove, the guide wire connecting section and the catheter connecting section being capable of moving toward and away from each other along an extending direction of the guide wire accommodation groove and the catheter accommodation groove, then the guide wire can be inserted into the catheter by accommodating the guide wire into the guide wire accommodating section and moving the guide wire connecting section and the catheter connecting section toward each other in a state in which the catheter is accommodated in the catheter accommodating groove.

If the grasping section includes a grasping member capable of moving toward and away from the guide wire to grasp or release the guide wire, and an elastic member for biasing the grasping member and the grasping member has a contacting portion which contacts the guide wire by elastic force of the elastic member, and a receiving portion for receiving force by the movement of the guide wire connecting section and the catheter connecting section toward each other to move the contacting portion away from the guide wire, then it is possible to move, while the elastic force of the elastic member is utilized to grasp the guide wire by means of the contacting portions, the guide wire connecting section and the catheter connecting section toward each other to move the contacting portions away from each other thereby to release the guide wire.

If a pair of such grasping members are connected for pivotal motion relative to each other by a turning shaft portion and the contacting portion is formed on one end portion side of each of the grasping members with respect to the turning shaft portion and the receiving portion is formed on the other end portion side of each of the grasping members with respect to the turning shaft portion, then by pressing the receiving portions, the contacting portions can be moved away from the guide wire.

If the catheter connecting section further includes a pressing portion for moving toward the guide wire connecting section to press the receiving portions toward a direction in which the guide wire is accommodated and the grasping members are turned around the turning shaft portion by being pressed at the receiving portions thereof so that the contacting sections move away from the guide wire, then it is possible to press the receiving portions in an interlocked relationship with the movement of the catheter connecting section and the guide wire connecting section toward each other to move the contacting portions away from the guide wire.

If the catheter connecting section further includes a pressing portion for moving toward the guide wire connecting section to press the receiving portions toward an opposite direction to a direction in which the guide wire is accommodated and, when the grasping members are pressed at the receiving portions thereof, the connection thereof by the turning shaft portion is cancelled and the contacting sections are moved away from the guide wire, then it is possible to press the receiving portions in an interlocking relationship with the movement of the catheter connecting section and the guide wire connecting section toward each other to move the contacting portions away from the guide wire.

If the device for the medical treatment further includes a restraining section adapted to restrain relative movement of the guide wire connecting section and the catheter connecting section, then it becomes easy to use the device for the medical treatment as a turning force applying tool which applies turning force to the guide wire in a state in which the guide wire is connected to the guide wire connecting section. Also it is possible to maintain the state in which the guide wire connecting section and the catheter connecting section are positioned closely to each other.

DETAILED DESCRIPTION OF THE PREFERRED EMBODIMENTS

In the following, embodiments of the present invention are described with reference to the drawings. It is to be noted that the dimensional ratio of the drawings is sometimes exaggerated and different from an actual ratio for the convenience of illustration.

First Embodiment

A device for the medical treatment according to a first embodiment of the present invention is a device having both of a function as a turning force applying tool for applying turning force to a guide wire 3 and an introduction assisting tool (inserter) for inserting an end portion of the guide wire 3 into an opening of a catheter 4.

The present device for the medical treatment includes, as shown in FIGS. 1 to 6, a guide wire connecting section 1 which can connect a portion of the guide wire 3 in the proximity of a proximal end, and a catheter connecting section 2 which can connect the distal end of a catheter 4, and the guide wire connecting section 1 and the catheter connecting section 2 are connected for relative movement toward and away from each other. It is to be noted that the distal end signifies an end portion (left end in FIG. 1) positioned on the side to be inserted into a blood vessel upon use, and the proximal end signifies an and portion (right end in FIG. 1) positioned on the user side who operates upon use.

The guide wire connecting section 1 includes a base 10 slidable with the catheter connecting section 2, and a grasping section 20 disposed on the base 10 for grasping the guide wire 3. A guide wire accommodating groove 11 is formed in a sidewardly open state on the base 10 such that it extends from the distal end to the proximal end for accommodating the guide wire 3, and the grasping section 20 is disposed on the face of the base 10 on which the guide wire accommodating groove 11 is formed. It is to be noted that the term sidewardly represents a direction perpendicular to the axial direction of the guide wire 3 and the catheter 4 connected to the device for the medical treatment.

The grasping section 20 includes a so-called "clothespin"-like structure and includes a pair of grasping members 21A and 21B for contacting with and grasping the guide wire 3, and an elastic member 22 for biasing the grasping members 21A and 21B so that the grasping members 21A and 21B press the guide wire 3.

The grasping members 21A and 21B are connected for pivotal motion relative to each other by a pivot shaft portion 23 provided substantially centrally. An arcuate shaft portion 23A of a predetermined thickness is formed on the grasping member 21A while an arcuate bearing portion 23B is provided in a shape of a groove on the other grasping member 21B such that it holds the shaft portion 23A of a predetermined thickness in a sandwiching manner and receives the arcuate face of the shaft portion 23A for sliding movement thereon (refer to FIG. 10). Consequently, according to the grasping members 21A and 21B in pair, the shaft portion 23A can turn in the bearing portion 23B, and the grasping members 21A and 21B can be separated from each other by moving the shaft portion 23A away from the bearing portion 23B.

A pair of contacting portions 24A and 24B which contact the guide wire 3 are formed on one end side (distal end side) of the grasping members 21A and 21B with respect to the pivot shaft portion 23, respectively. Further, a pair of receiving portions 25A and 25B are formed on the other end side (proximal end side) of the grasping members 21A and 21B with respect to the pivot shaft portion 23 such that they receive force when the catheter connecting section 2 comes near.

The elastic member 22 is a wire member of an arcuate shape made of an elastic material and extends through the grasping members 21A and 21B on the receiving side with respect to the pivot shaft portion 23. The elastic member 22 presses, at the opposite end portions thereof, the grasping members 21A and 21B such that the contacting portion sides of the grasping members 21A and 21B with respect to the pivot shaft portion 23 move toward each other (direction in which the contacting portion sides move toward the guide wire 3). If one of the receiving portions 25A and 25B in pair is pressed so that the receiving portions 25A and 25B move toward each other, then the contacting portions 24A and 24B can be moved away from each other against the biasing force of the elastic member 22. And, the elastic member 22 is fixed at a central portion thereof to an elastic member fixing portion 12 which is formed on the bottom face of the guide wire accommodating groove 11 of the base 10 and covers the elastic member 22. In particular, the elastic member 22 is configured such that it extends through the elastic member fixing portion 12 formed on the bottom face of the guide wire accommodating groove 11. Accordingly, also when the guide wire 3 is accommodated into the guide wire accommodating groove 11, the elastic member 22 is positioned lower than the guide wire 3 and does not interfere with the guide wire 3. The grasping members 21A and 21B are fixed to the base 10 only at the elastic member fixing portion 12, and accordingly, if the contacting portions 24A and 24B are moved away from each other against the pressing force of the elastic member 22 and further the shaft portion 23A and the bearing portion 23B are moved away from each other, then the guide wire 3 accommodated in the guide wire accommodating groove 11 can be released sidewardly (in an upward direction of the plane of FIG. 11) from the guide wire accommodating groove 11.

Although the base 10 is formed from a resin material, if the grasping members 21A and 21B are held by the base 10 and sliding movement of the base 10 with respect to the catheter connecting section 2 is possible, then the material thereof is not limited particularly, but the base 10 may be formed, for example, from a metal material or a paper board stuck together.

Although the grasping members 21A and 21B are formed from a resin material, if the function of grasping the guide wire 3 can be exhibited, then the material thereof is not limited particularly, but they may be formed, for example, from a metal material or a paper board stuck together.

As a resin material (synthetic resin) applied to the base 10 and the grasping members 21A and 21B, a hard resin or a semi hard resin having a rigidity of such a degree that it does not block off when it is held by a finger, and as such material, polyolefin (polyethylene, polypropylene), styrene-based resin (polystyrene, MS resin), polyester, polycarbonate, hard vinyl chloride resin and so forth are used suitably. As a metal material, stainless steel, aluminum, copper, ion, nickel, titanium and so forth can be used.

The elastic member 22 is formed from a metal material, and stainless steel, aluminum, copper, ion, nickeltitanium and so forth are suitably used. It is to be noted that the material is not limited particularly if it exhibits elasticity so that a function of biasing the grasping members 21A and 21B can be exhibited, and they may be formed, for example, from a synthetic resin or a paper board stuck together which can be applied also to the base 10 and the grasping members 21A and 21B.

The catheter connecting section 2 may include a main body member 30 in the inside of which an accommodation section 33 in which the base 10 can be accommodated for sliding movement of the same is formed, and a catheter holding member 40 in which a catheter accommodating groove 41 in which the catheter 4 can be accommodated and held is formed.

The main body member 30 has a circular cylindrical portion 31 of a circular cylinder shape formed on the distal end side thereof which is pinched with fingers by an operator in order to apply turning force to the guide wire 3 connected to the guide wire connecting section 1. Further, the main body member 30 is cut off at part of the circular cylinder in a circumferential direction to form a circular cylinder proximal end portion 32 on the proximal end side of the circular cylindrical portion 31 such that the catheter holding member 40 is embedded in the circular cylinder proximal end portion 32. A slit 34 is formed to extend from the distal end side to the proximal end side in the circular cylindrical portion 31 such that it extends through the circular cylindrical portion 31 from an outer circumferential face to the accommodation section 33.

Figure 1:
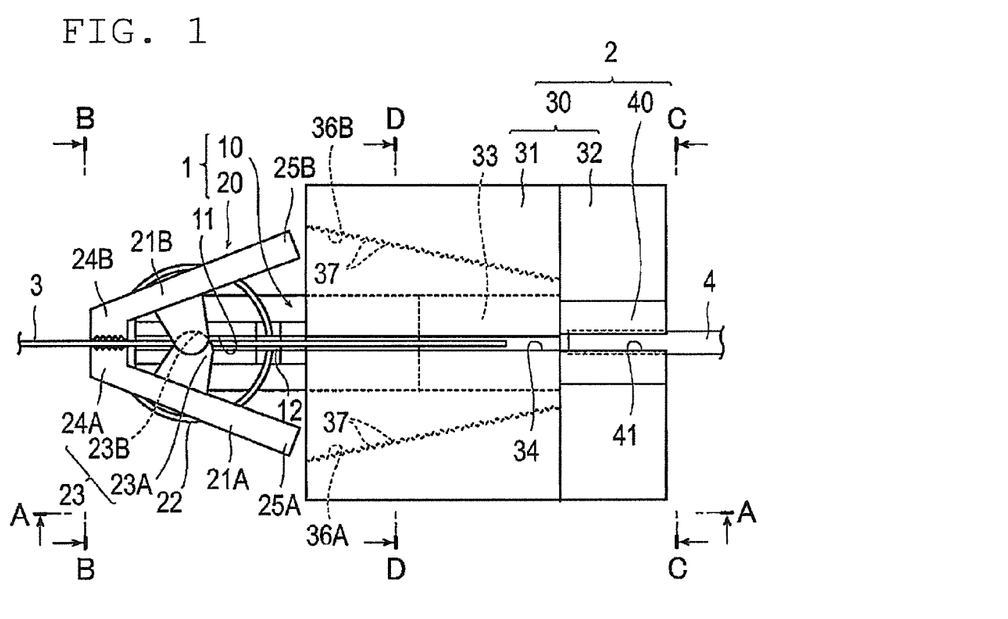
FIG. 1 is a top plan view of a device for the medical treatment according to a first embodiment of the present invention.
Figure 2:
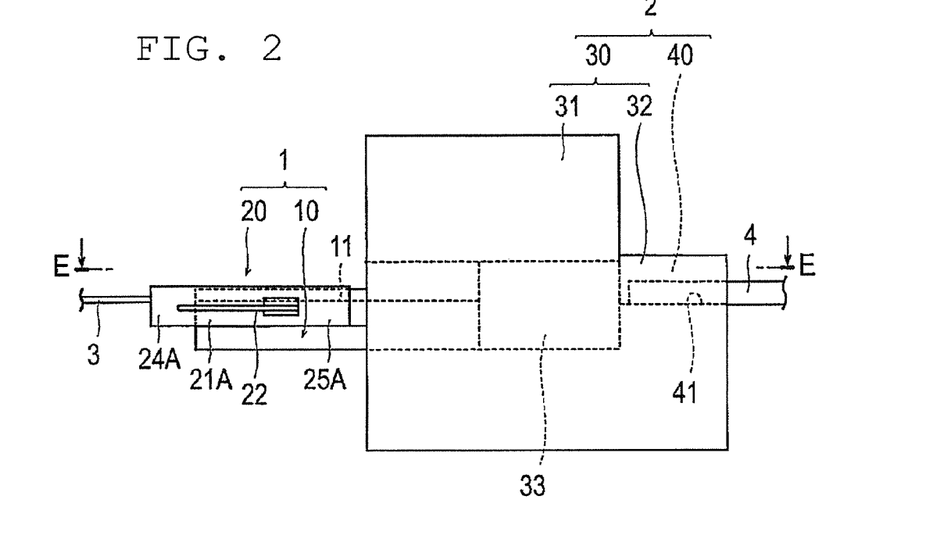
FIG. 2 is a view as viewed in a direction of an arrow mark along line A-A of FIG. 1.
Figure 3:
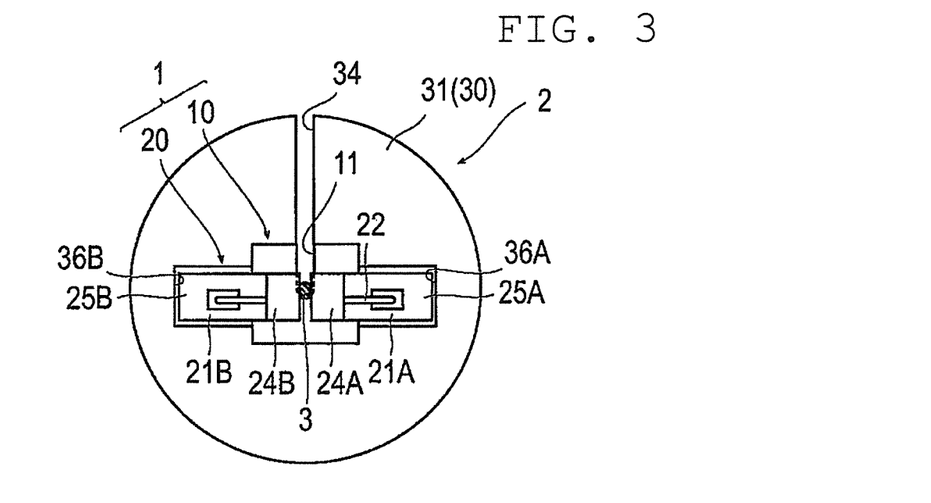
FIG. 3 is a view as viewed in a direction of an arrow mark along line B-B of FIG. 1.
Figure 4:
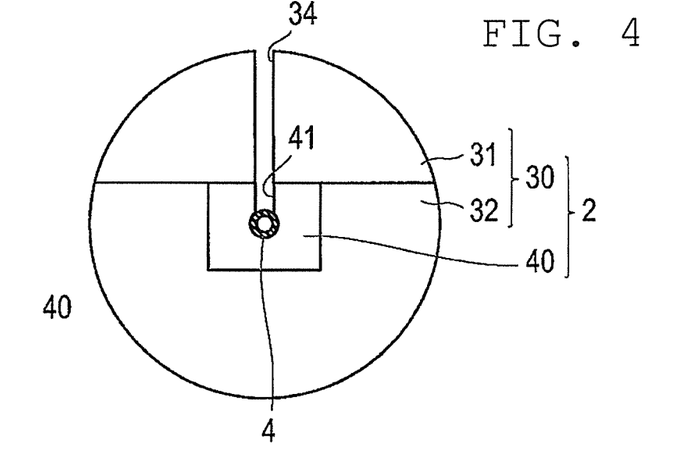
FIG. 4 is a view as viewed in a direction of an arrow mark along line C-C of FIG. 1.
Figure 5:
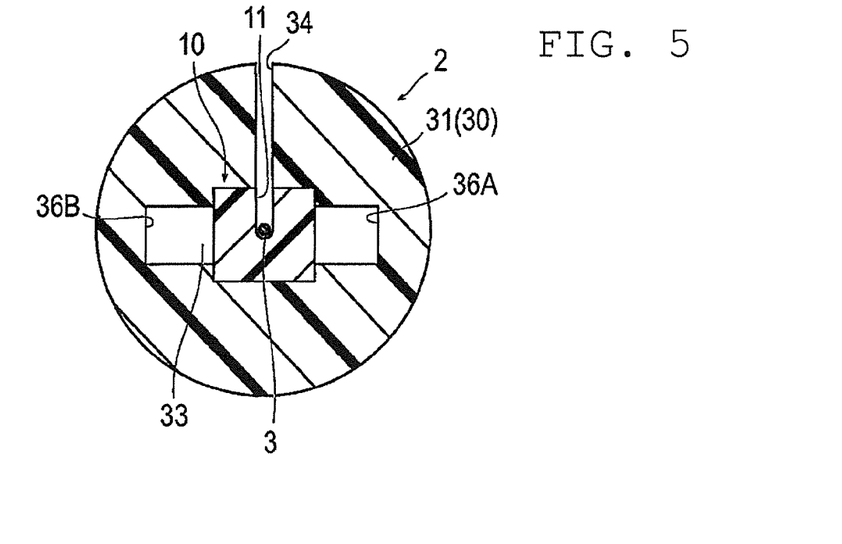
FIG. 5 is a sectional view taking along line D-D of FIG. 1.
Figure 6:
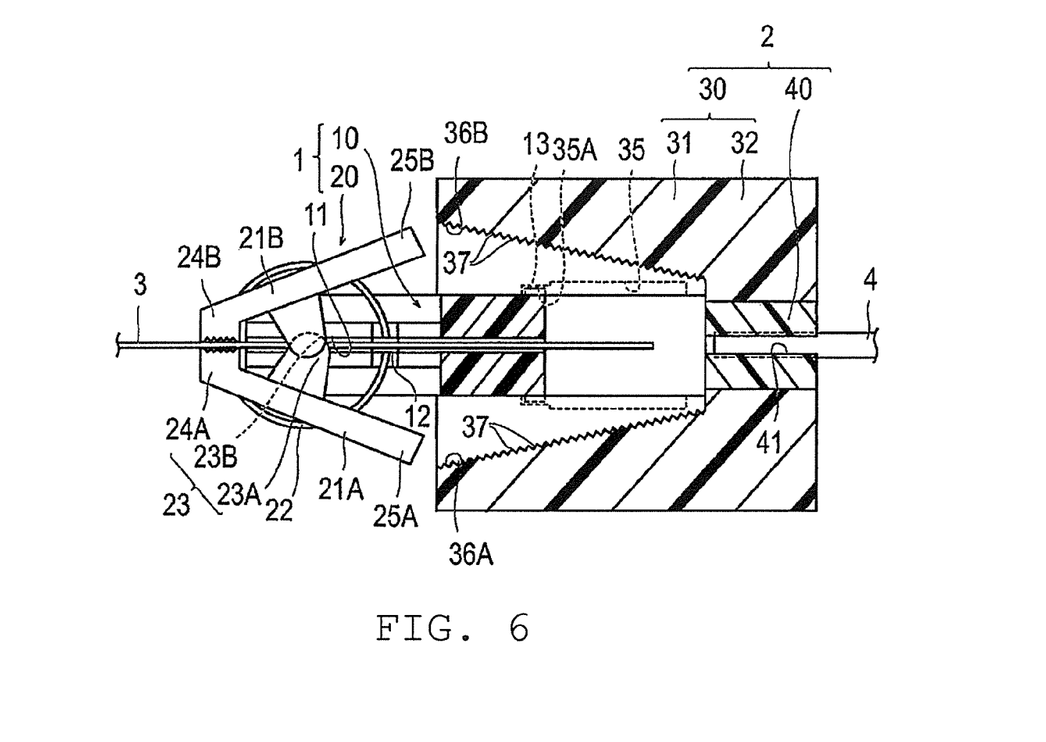
FIG. 6 is a sectional view taking along line E-E of FIG. 2.

The accommodation section 33 holds the base 10 for sliding movement thereon but does not turn relative to the base 10 so that turning force may be transmitted to the base 10. The accommodation section 33 is preferably structured such that it holds the base 10 such that the base 10 does not come off when the base 10 moves to the distal end side and can lock forward and backward movement of the base 10 with respect to the main body member 30 when the device for the medical treatment is used as the turning force applying tool. As an example, it is possible to form, as shown in FIG. 6, a projection 13 on a face on which the base 10 slidably moves and form a grooved portion 35 on the accommodation section 33 such that it accommodates the movement of the projection 13 within a fixed range. Further, by forming a restraining grooved portion 35A (restraining section) of a small depth on the distal end side of the grooved portion 35 such that the projection 13 is fitted in the restraining grooved portion 35A, the base 10 can be restrained with respect to the main body member 30.

Further, the accommodation section 33 can accommodate also the receiving portions 25A and 25B of the grasping members 21A and 21B, and pressing portions 36A and 36B of a tapering shape with which the receiving portions 25A and 25B contact when the catheter connecting section 2 and the guide wire connecting section 1 relatively move toward each other are formed. The pressing portions 36A and 36B are formed such that the width thereof gradually decreases toward the proximal end (such that the distance between the pressing portion 36A and the pressing portion 36B decreases), and accordingly, if the catheter connecting section 2 and the guide wire connecting section 1 move relatively toward each other, then the pressing portions 36A and 36B press the receiving portions 25A and 25B toward the guide wire accommodating groove 11 side, whereupon the contacting portions 24A and 24B of the grasping members 21A and 21B are opened (refer to FIG. 8). And, fine projection and recess portions 37 (restraining sections) are formed on the pressing portions 36A and 36B so that the receiving portions 25A and 25B contacting therewith may not slidably move back in the direction toward the distal end by the elastic force of the elastic member 22.

The catheter holding member 40 is formed from a material which is flexible to such a degree that it can push the catheter 4 into the catheter accommodating groove 41 from sidewardly and then take out the catheter 4 from the catheter accommodating groove 41. Thus, if the catheter 4 is pushed into the catheter accommodating groove 41, then the catheter 4 can be maintained in the held state by the elastic force of the catheter holding member 40. Although, to the catheter holding member 40, synthetic resins such as polyolefin (polyethylene, polypropylene), styrene-based resin (polystyrene, MS resin), polyester, polycarbonate and hard vinyl chloride resin, elastomer and so forth can be applied suitably, the material of the catheter holding member 40 is not limited to them.

The guide wire accommodating groove 11 and the catheter accommodating groove 41 of the base 10 extend coaxially such that the center axes of the guide wire 3 and the catheter 4 held thereby are juxtaposed on the same line, and all of the guide wire accommodating groove 11, catheter accommodating groove 41 and slit 34 coincide with each other in the direction in which they are open sidewardly.

Although the main body member 30 is formed from a resin material, if it can slidably move relative to the base 10 and can press the receiving portions 25A and 25B of the grasping members 21A and 21B, then the material thereof is not limited particularly, but the main body member 30 may be formed, for example, from a metal material or a paper board stuck together.

As a resin material (synthetic resin) applied to the base main body member 30, a hard resin or a semi hard resin having a rigidity of such a degree that it does not block off when it is held by a finger, and as such material, polyolefin (polyethylene, polypropylene), styrene-based resin (polystyrene, MS resin), polyester, polycarbonate, hard vinyl chloride resin and so forth are used suitably. As a metal material, stainless steel, aluminum, copper, ion, nickeltitanium and so forth can be used.

Now, action of the device for the medical treatment according to the present embodiment is described. Here, it is assumed that the catheter 4 into which the guide wire 3 is fitted is a micro catheter 4.

First, a sheath (introducer) is indwelled in a blood vessel of a patient, for example, by the Seldinger method, and a guide wire of a large diameter (for example, an outer diameter of 0.035 inches) for a guiding catheter is inserted into the blood vessel through the sheath. Then, the guide wire is pushed to advance in the blood vessel to precede until it reaches a target region (for example, the entrance of a coronary artery) and then the guiding catheter is pushed to advance in the blood vessel along the guide wire to the target region. Then, the guiding catheter is engaged with the target region. Thereafter, the guide wire for the guiding catheter is drawn off while the guiding catheter is left.

Figure 7:
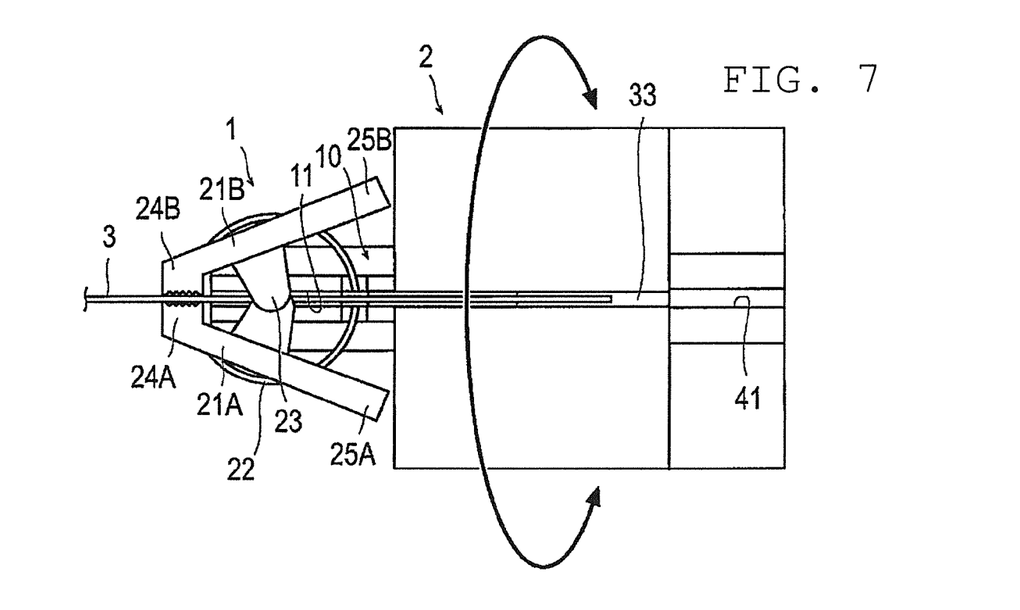
FIG. 7 is a top plan view illustrating a case in which the device for the medical treatment according to the first embodiment is used as a turning force applying tool.

Then, in a state in which the device for the medical treatment according to the present embodiment is connected to the proximal end side of the guide wire 3 of a small diameter (for example, an outer diameter of 0.016 inches) for the micro catheter 4, the guide wire 3 is inserted from the proximal end side of the guiding catheter. At this time, a portion of the guide wire 3 in the proximity of the proximal end is accommodated in the guide wire accommodating groove 11 of the base 10 as shown in FIG. 7, grasped by the grasping members 21A and 21B, and is further held by the pivot shaft portion 23 against sideward release from the guide wire accommodating groove 11. Then, a proximal end side end portion of the guide wire 3 is positioned in the accommodation section 33 on the proximal end side with respect to a proximal end side end portion of the base 10. In order to connect the guide wire 3 to the device for the medical treatment in this manner, the guide wire connecting section 1 and the catheter connecting section 2 are moved away from each other first, and the receiving portions 25A and 25B of the grasping members 21A and 21B are pushed in with fingers to move the contacting portions 24A and 24B away from each other. In this condition, the proximal end side end portion of the guide wire 3 is inserted from the distal end side of the guide wire accommodating groove 11. Then, in a state in which the proximal end side end portion of the guide wire 3 passes the base 10 and reaches the accommodation section 33, the pushing of the receiving portions 25A and 25B is canceled to establish a state in which the guide wire 3 is grasped by the contacting portions 24A and 24B. It is to be noted that the working of connecting the guide wire 3 to the device for the medical treatment is preferably carried out in advance before the manipulation is started.

Thereafter, while turning force is applied to the guide wire 3 advanced from the distal end side of the guiding catheter into the blood vessel by means of the device for the medical treatment to operate the guide wire 3, the guide wire 3 is advanced in the direction toward the distal end to introduce the guide wire 3 to the target region (for example, to a lesion portion in the coronary artery). In particular, since the guide wire 3 can be grasped by the device for the medical treatment such that turning force can be applied, the device for the medical treatment can be used as a turning force applying tool.

Figure 8:
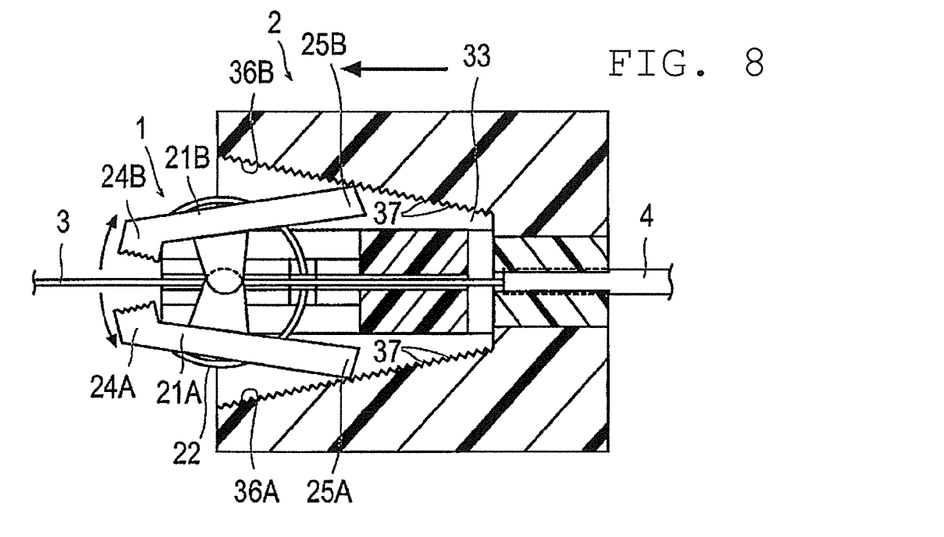
FIG. 8 is a sectional view corresponding to a section along line E-E of FIG. 2 and illustrating a case in which a guide wire connecting section and a catheter connecting section are moved toward each other.

Then, the micro catheter 4 is pushed sidewardly into and fixed to the catheter accommodating groove 41 of the device for the medical treatment. At this time, since the guide wire accommodating groove 11 and the catheter accommodating groove 41 are positioned coaxially, the openings of the guide wire 3 and the micro catheter 4 are positioned on the same line. Then, if the guide wire connecting section 1 and the catheter connecting section 2 are relatively moved toward each other so that the base 10 is accommodated into the accommodation section 33, then the guide wire 3 and the micro catheter 4 held thereon, respectively, move toward each other as shown in FIG. 8 and the guide wire 3 is inserted into the opening of the micro catheter 4. In particular, the device for the medical treatment not only has a function as a turning force applying tool but also has a function as an introduction assisting tool for inserting an end portion of the guide wire 3 into the opening of the micro catheter 4. Accordingly, the necessity to use both of a turning force applying tool and an instruction assisting tool separate from each other is eliminated, and the workability is improved. Further, since an end portion of the guide wire 3 can be inserted into the opening of the micro catheter 4 in an interlocking relationship with an operation for relatively moving the guide wire connecting section 1 and the catheter connecting section 2 toward each other, the device for the medical treatment is superior in operability.

Then, when the guide wire connecting section 1 and the catheter connecting section 2 relatively move toward each other, the receiving portions 25A and 25B formed on the grasping members 21A and 21B come to the pressing portions 36A and 36B of a tapering shape formed on the accommodation section 33 and are pressed in a direction in which the guide wire 3 is positioned by the pressing portions 36A and 36B. Consequently, the grasping members 21A and 21B are pivoted around the pivot shaft portion 23 against the elastic force of the elastic member 22, whereupon the contacting portions 24A and 24B are spaced away from each other to cancel the grasping of the guide wire 3. It is to be noted that, when the grasping of the guide wire 3 is canceled, the proximal end side end portion of the guide wire 3 is already inserted in the opening of the micro catheter 4. Then, since the projection and recess portions 37 are formed on the pressing portions 36A and 36B, if the movement of the guide wire connecting section 1 and the catheter connecting section 2 toward each other is stopped, then the receiving portions 25A and 25B are restrained by the pressing portions 36A and 36B, and consequently, the relative positions of the catheter connecting section 2 and the guide wire connecting section 1 can be maintained fixed. In other words, the pressing portions 36A and 36B and the receiving portions 25A and 25B achieve also a function as a restraining section for restraining relative movement of the catheter connecting section 2 and the guide wire connecting section 1.

Figure 9:
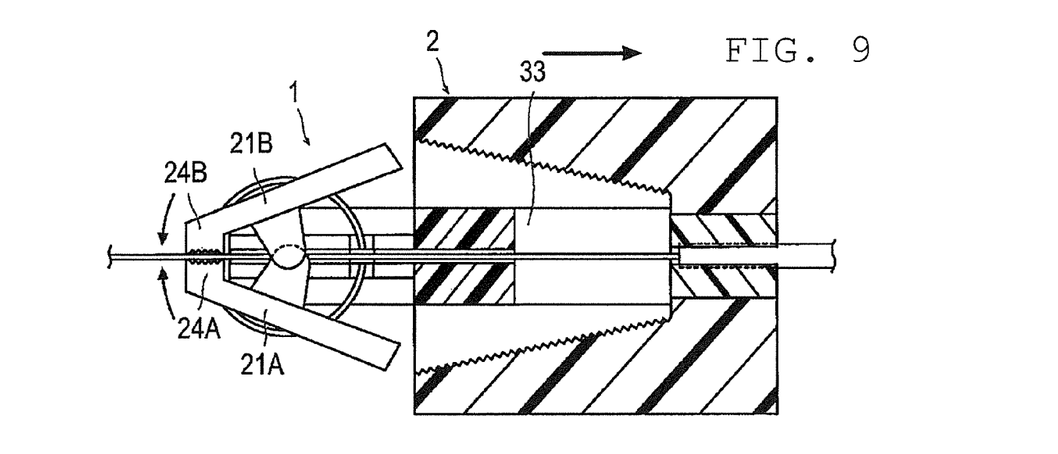
FIG. 9 is a sectional view corresponding to the section taking along line E-E of FIG. 2 and illustrating a case in which the guide wire connecting section and the catheter connecting section are moved away from each other.
Figure 10:
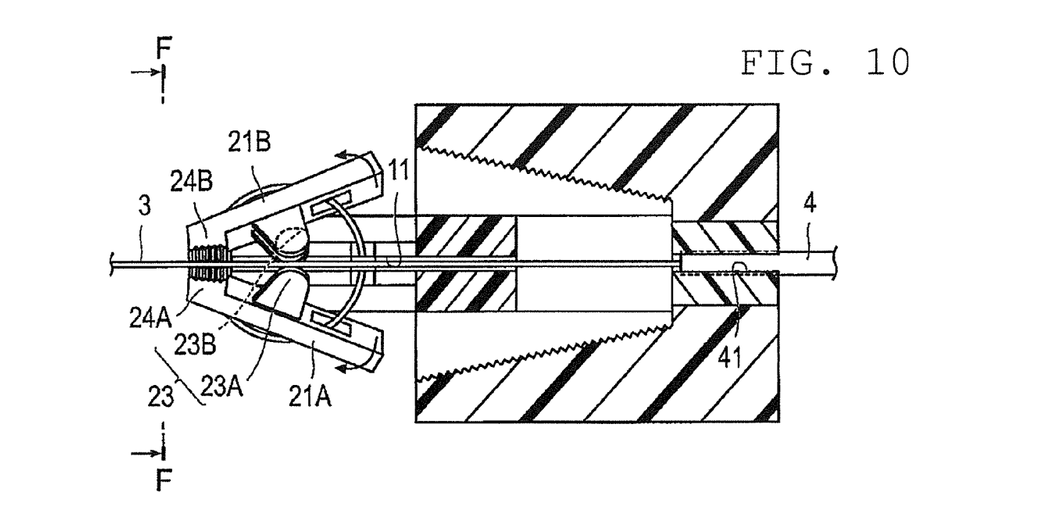
FIG. 10 is a sectional view corresponding to the section along line E-E of FIG. 2 and illustrating a case in which a guide wire is taken out from the guide wire connecting section.
Figure 11:
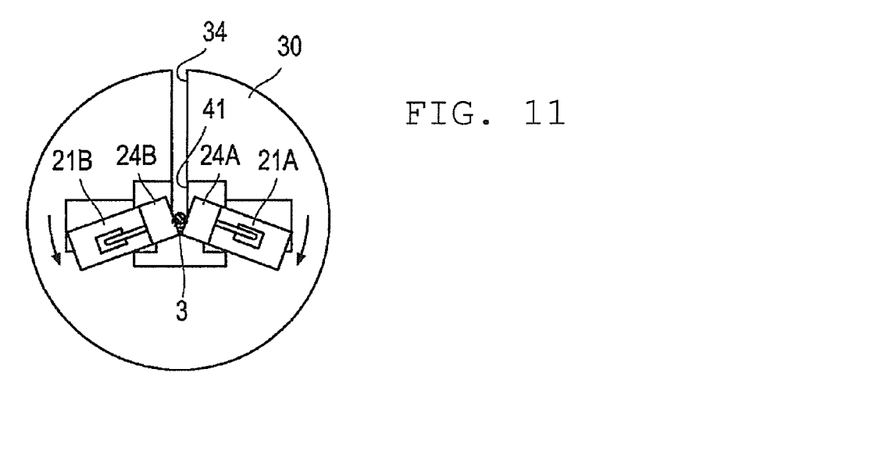
FIG. 11 is a view as viewed in a direction of an arrow mark along line F-F of FIG. 10.

Then, the micro catheter 4 is advanced in a direction toward the distal end with respect to the guide wire 3 together with the device for the medical treatment until the guide wire 3 is led out from a hub portion 4A formed on the proximal end side of the micro catheter 4. Thereafter, the catheter connecting section 2 and the guide wire connecting section 1 are relatively moved away from each other as shown in FIG. 9 until the grasping members 21A and 21B are projected from the accommodation section 33. Consequently, the contacting portions 24A and 24B grasp the guide wire 3. Then, if the grasping members 21A and 21B are twisted in the opposite directions to each other as shown in FIGS. 10 and 11 to move the contacting portions 24A and 24B away from each other against the pressing force by the elastic member 22 and then move the shaft portion 23A and the bearing portion 23B away from each other, then the guide wire 3 accommodated in the guide wire accommodating groove 11 can be released sidewardly from the guide wire accommodating groove 11. Then, if, in this state, the distal end portion of the micro catheter 4 is removed from the catheter accommodating groove 41, then the micro catheter 4 in a state in which the guide wire 3 is fixed therein can be taken out sidewardly from the device for the medical treatment through the slit 34 of the main body member 30. It is to be noted that, although the guide wire 3 and the micro catheter 4 may be taken out sidewardly from the device for the medical treatment before the guide wire 3 is led out from the hub portion 4A of the micro catheter 4, when the guide wire 3 and the micro catheter 4 are taken out from the device for the medical treatment, preferably the guide wire 3 is inserted in the micro catheter 4 to such a degree that the guide wire 3 does not come off from the micro catheter 4.

Figure 12:
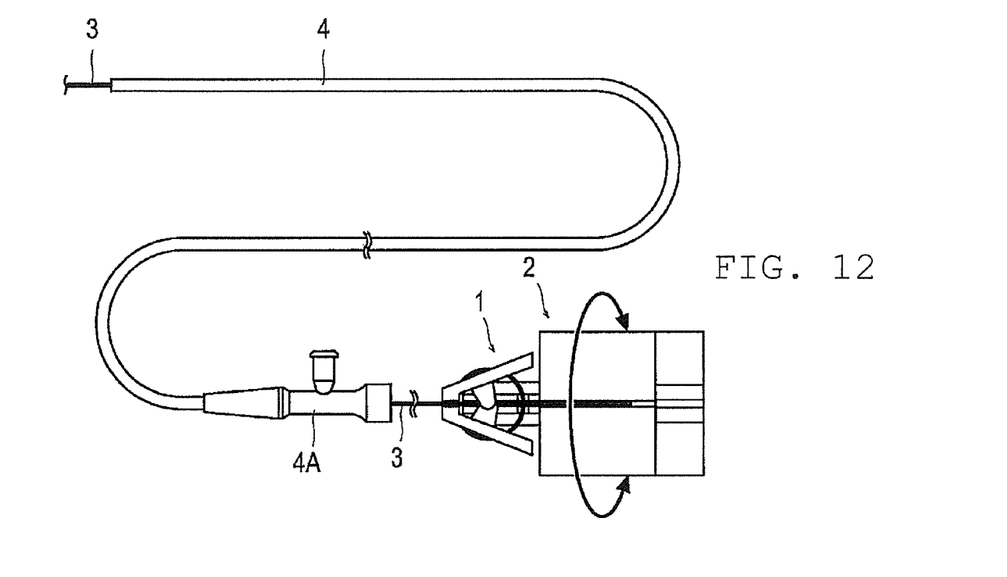
FIG. 12 is a top plan view illustrating a case in which the guide wire led out from a hub portion of a catheter is grasped by the device for the medical treatment.
Figure 13:
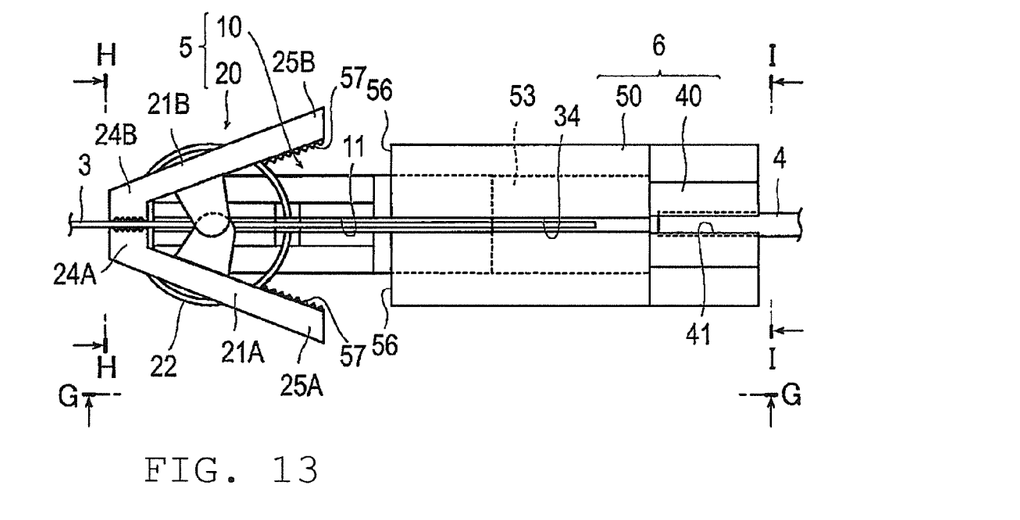
FIG. 13 is a top plan view of a device for the medical treatment according to a second embodiment of the present invention.
Figure 14:
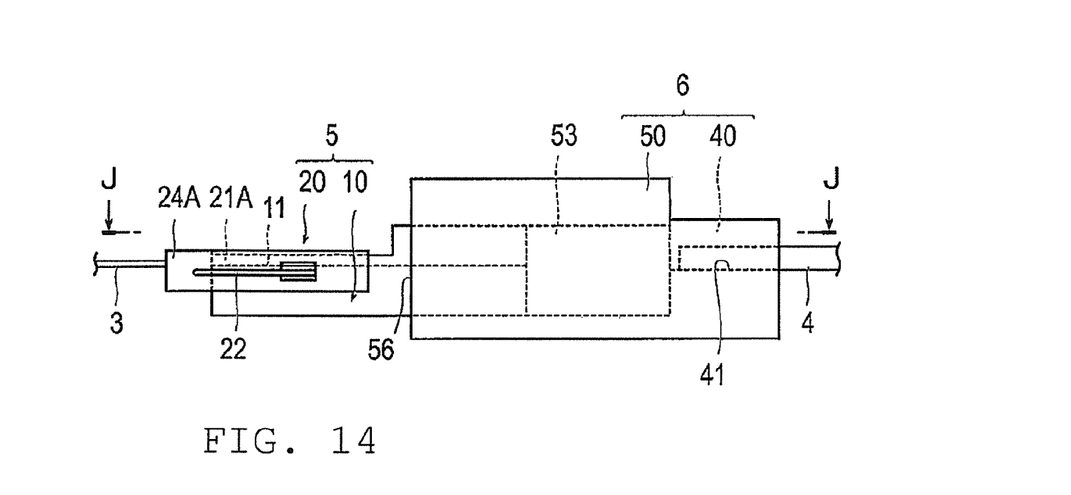
FIG. 14 is a view as viewed in a direction of an arrow mark along line G-G of FIG. 13.
Figure 15:
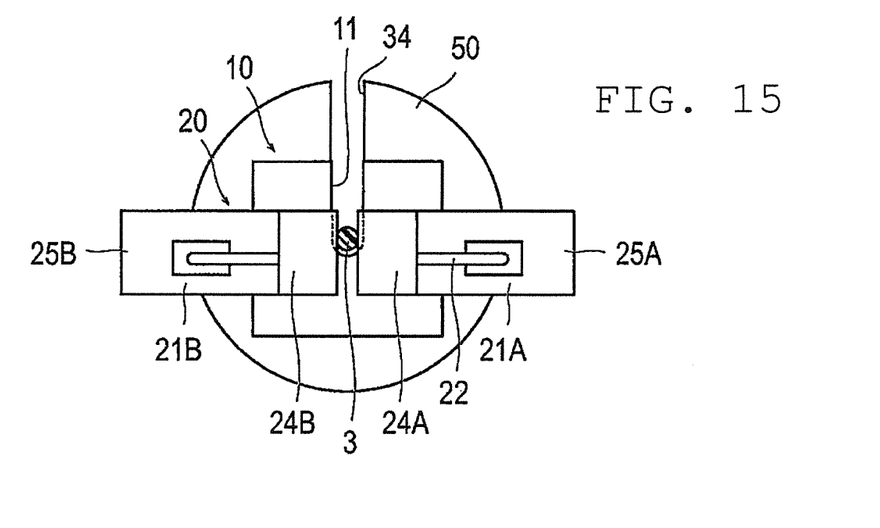
FIG. 15 is a view as viewed in a direction of an arrow mark along line H-H of FIG. 13.
Figure 16:
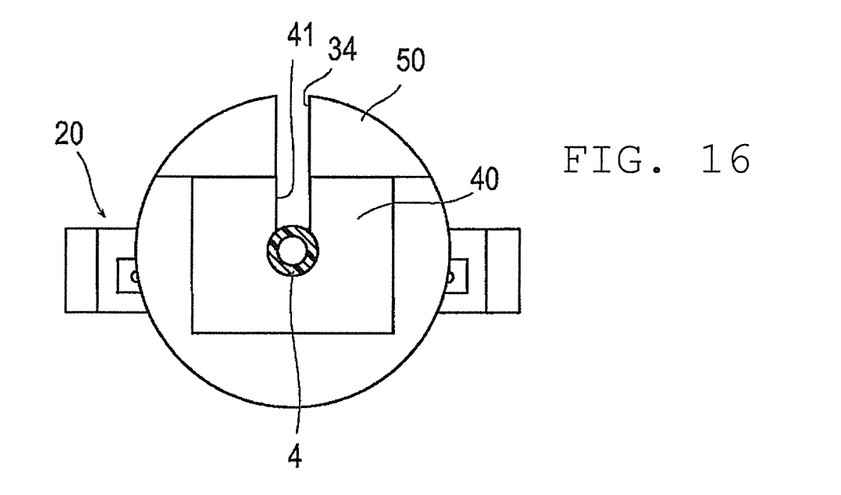
FIG. 16 is a view as viewed in a direction of an arrow mark along line I-I of FIG. 13.
Figure 17:
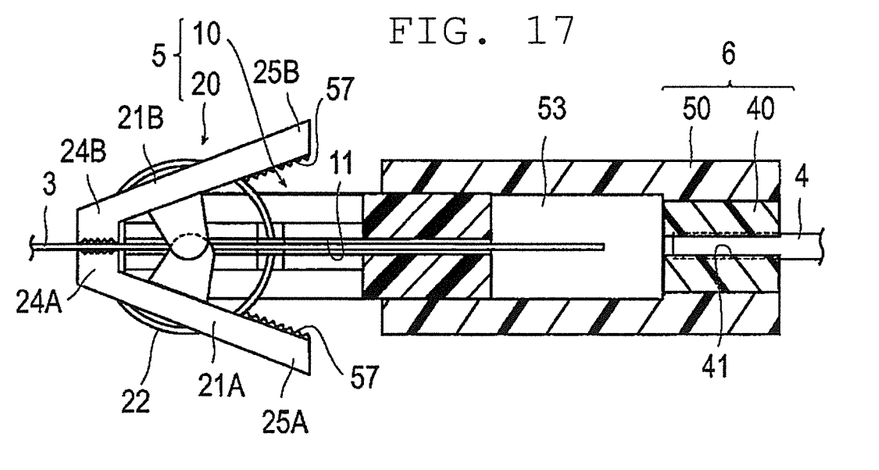
FIG. 17 is a sectional view taken along line J-J of FIG. 14.

Thereafter, as shown in FIG. 12, it is possible to move and position the device for the medical treatment to and at the proximal end portion of the guide wire 3 projecting from the hub portion 4A of the micro catheter 4 and use the device for the medical treatment as a turning force applying tool which can apply turning force to the guide wire 3. Thereafter, the micro catheter 4 and the guide wire 3 would be operated to carry out a medical treatment of the target region.

Second Embodiment

A device for the medical treatment according to a second embodiment of the present invention is different from the device for the medical treatment according to the first embodiment in the configuration for causing the grasping members 21A and 21B to operate. It is to be noted that members having functions similar to those of the device for the medical treatment according to the first embodiment are denoted by like reference characters and description thereof is omitted.

As shown in FIGS. 13 to 17, in the device for the medical treatment according to the second embodiment, a tapering pressing portion is not formed on the accommodation section 53 on which the base 10 slidably moves in the inside of a main body member 50, but a pressing portion 56 is formed at an edge portion on the distal end side of an outer peripheral face of the main body member 50. And, projection and recess portions 57 (restraining sections) are formed on mutually opposing faces of the receiving portions 25A and 25B of the grasping members 21A and 21B. Since the elastic member 22 is positioned below the guide wire accommodating groove 11 (in a depthwise direction of the groove), the grasping members 21A and 21B are positioned generally in a downwardly displaced relationship from the center of the main body member 50.

In the device for the medical treatment according to the second embodiment, if the guide wire 3 is grasped by the grasping section 20 similarly as in the first embodiment in a state in which a guide wire connecting section 5 and a catheter connecting section 6 are spaced from each other, then the device for the medical treatment according to the second embodiment can be used as a turning force applying tool.

Figure 18:
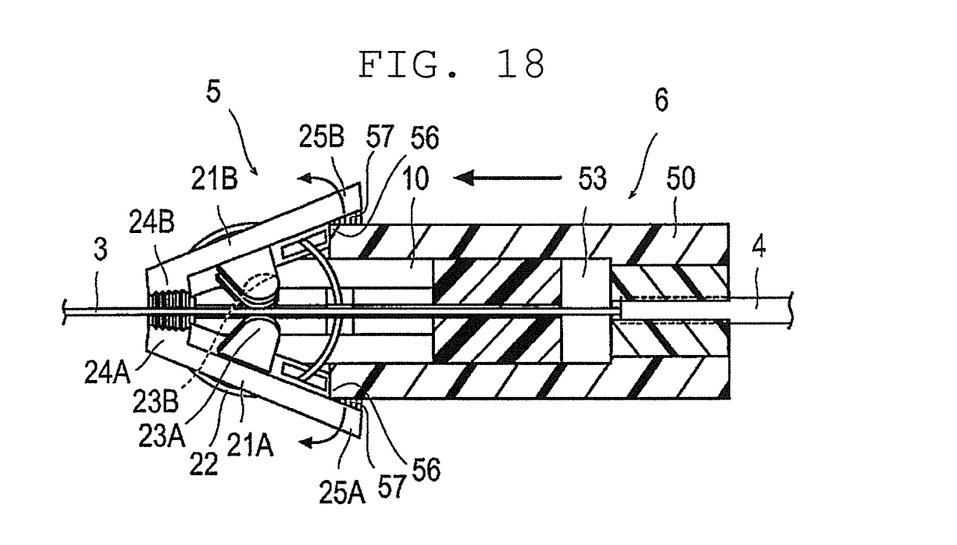
FIG. 18 is a sectional view corresponding to the section taken along line J-J of FIG. 14 and illustrating a case in which a guide wire connecting section and a catheter connecting section of the device for the medical treatment according to the second embodiment are moved toward each other.

Then, if the guide wire connecting section 5 and the catheter connecting section 6 are relatively moved toward each other so that the base 10 is accommodated into the accommodating section 53, then the guide wire 3 and the micro catheter 4 held on the guide wire connecting section 5 and the catheter connecting section 6 move toward each other until the guide wire 3 is inserted into the opening of the micro catheter 4 as shown in FIG. 18. In particular, the device for the medical treatment functions as an introduction assisting apparatus for inserting an end portion of the guide wire 3 into the opening of the micro catheter 4.

Then, as the guide wire connecting section 5 and the catheter connecting section 6 relatively move toward each other, the receiving portions 25A and 25B formed on the grasping members 21A and 21B come to the pressing portion 56 formed on the main body member 50 and are pressed by the pressing portion 56 in a direction in which they are spaced away from the guide wire 3, that is, in such a manner that they are pushed open. At this time, since the grasping members 21A and 21B are positioned in a downwardly displaced relationship from the center of the main body member 50, the pressing member 56 with which the receiving portions 25A and 25B contact is positioned on the lower side of an outer peripheral face of the circular cylinder shape of the main body member 50. Therefore, if the catheter connecting section 6 and the guide wire connecting section 5 are relatively moved toward each other, then the grasping members 21A and 21B are acted upon by force from the pressing portion 56 such that the upper sides of the receiving portions 25A and 25B of the grasping members 21A and 21B are opened by a great amount, whereupon the grasping members 21A and 21B are twisted in the opposite directions to move the contacting portions 24A and 24B away from each other against the pressing force of the elastic member 22, and further, the shaft portion 23A and the bearing portion 23B are moved away from each other. Consequently, the grasping of the guide wire 3 by the contacting portions 24A and 24B is canceled, and the guide wire 3 accommodated in the guide wire accommodating groove 11 is placed into a state in which it can be released sidewardly from the guide wire accommodating groove 11. In other words, the present device for the medical treatment can place the guide wire 3 into a sidewardly releasable state in an interlocked relationship with an operation of relatively moving the guide wire connecting section 5 and the catheter connecting section 6 toward each other, and is superior in workability. It is to be noted that, when the grasping of the guide wire 3 is cancelled, the proximate end side end portion of the guide wire 3 is inserted in the opening of the micro catheter 4 already. And, since the projection and recess portions 37 (restraining section) are formed on the receiving portions 25A and 25B, even if the movement of the guide wire connecting section 5 and the catheter connecting section 6 toward each other stops, the pressing portion 56 is restrained by the receiving portions 25A and 25B. Consequently, the relative positions of the catheter connecting section 6 and the guide wire connecting section 5 can be maintained fixed. In other words, the pressing portion 56 and the receiving portions 25A and 25B achieve also a function as a restraining section for restraining relative movement of the catheter connecting section 6 and the guide wire connecting section 5.

Then, if, in this state, the distal end portion of the micro catheter 4 is released from the catheter accommodating groove 41, then the micro catheter 4 in the state in which the guide wire 3 is fitted therein can be taken out sidewardly from the device for the medical treatment through the slit 34 of the main body member 50.

Also the device for the medical treatment according to the second embodiment not only has a function as a turning force applying tool but also has a function as an introduction assisting tool for inserting an end portion of the guide wire 3 into the opening of the micro catheter 4. Accordingly, the necessity to use both of a turning force applying tool and an instruction assisting tool separate from each other is eliminated, and the workability is improved. Further, since an end portion of the guide wire 3 can be inserted into the opening of the micro catheter 4 in an interlocking relationship with an operation for relatively moving the guide wire connecting section 5 and the catheter connecting section 6 toward each other, the device for the medical treatment is superior in operability.

It is to be noted that the present invention is not limited to the embodiments described above but can be modified in various manners within the scope of the claims. For example, the configuration of the grasping section for grasping a guide wire is not limited particularly if it can cancel its grasping of a guide wire by relatively moving the guide wire connecting portion and the catheter connecting portion toward each other. Accordingly, while, for example, in the first embodiment, the contacting portions 24A and 24B of the grasping members 21A and 21B are positioned on the distal end side and the receiving portions 25A and 25B are positioned on the proximal end side, also it is possible to adopt a reverse configuration. Further, not the configuration wherein the grasping section includes a pair of grasping member for sandwiching the guide wire 3 but another configuration wherein the grasping section is configured from one grasping member, by which the guide wire 3 is pressed.

Figure 19:
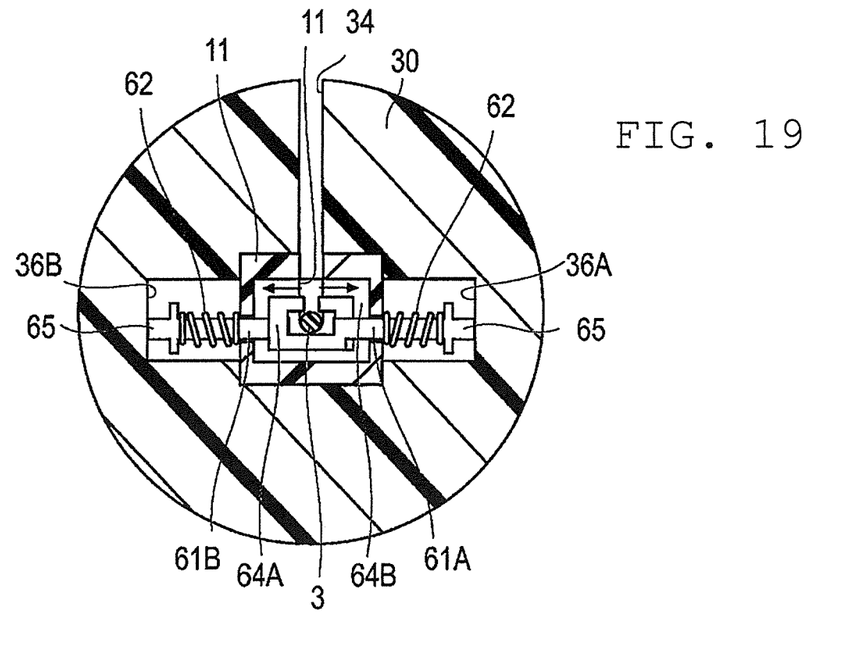
FIG. 19 is a sectional view showing another example of a grasping section of the first embodiment.

On the other hand, while FIG. 19 shows another example of the grasping section of the first embodiment is shown in a sectional view perpendicular to the center axis of the guide wire 3, a pair of grasping members 61A and 61B are biased by an elastic member 62 in directions in which they are moved away from each other and the guide wire 3 is grasped by contacting portions 64A and 64B of a hooked shape. With the grasping members 61A and 61B, when receiving portions 65 of the grasping members 61A and 61B are pressed by the pressing portions 36A and 36B, the grasping members 61A and 61B in pair move toward each other while the contacting portions 64A and 64B of a hooked shape move to cancel the grasping of the guide wire 3, and the guide wire 3 accommodated in the guide wire accommodating groove 11 is placed into a state in which it can be released sidewardly from the guide wire accommodating groove 11.

Or, an inlet port of a funnel shape open toward the distal end side may be formed on the distal end side of the catheter accommodating groove 41 so as to facilitate insertion of the guide wire 3 into the opening of the catheter 4.

What is claimed is:

1. A tool for turning a guide wire and for inserting the guide wire in a catheter in a distal-to-proximal direction, the tool comprising:
   a gripping portion configured for securely holding the guide wire;
   a receiving portion configured for securely receiving a distal end of the catheter therein to be aligned with the held guide wire, the receiving portion being disposed proximally to the gripping portion; and
   cooperating portions of the gripping and receiving portions configured to allow for relative shifting of the gripping and receiving portions toward and away from each other while maintaining the alignment between the guide wire and catheter for introducing and fitting the guide wire in a distal end opening of the catheter upon relative shifting of the gripping and receiving portions toward each other and including restraining structure that keeps the gripping and receiving portions non-rotatably engaged with each other upon relative shifting of the gripping and receiving portions towards each other for allowing the receiving portion to be used to apply a turning force to the held guide wire.

2. The tool of claim 1 wherein the cooperating portions include a base member of the gripping portion having at least one guide wire grasping member carried thereon for securely holding the guide wire, and a main body member of the receiving portion having an opening sized to fit the base member therein for non-rotatable, linear sliding in the opening for fitting the guide wire into the catheter and so that turning of the receiving portion applies a turning force to the guide wire.

3. The tool of claim 2 wherein the base member and the opening of the main body member include abutment structure therebetween that defines the limit of the linear shifting between the base member and the main body member in the opening thereof.

4. The tool of claim 1 wherein the gripping portion comprises at least one guide wire grasping member and a biasing mechanism that provides a bias force to urge the grasping member into engagement with the guide wire for securely holding the guide wire.

5. The tool of claim 4 wherein the at least one guide wire grasping member comprises a pair of guide wire grasping members each having a guide wire contacting end portion and being pivotal relative to each other with the biasing mechanism comprising a biasing member between the grasping members that urges the grasping members to pivot so that the contacting end portions shift toward each other to securely engage and hold the guide wire therebetween.

6. A tool for turning a guide wire and for inserting the guide wire in a catheter, the tool comprising:
- a gripping portion configured for securely holding the guide wire;
- a receiving portion configured for securely receiving a distal end of the catheter therein to be aligned with the held guide wire; and
- cooperating portions of the gripping and receiving portions configured to allow for relative shifting of the gripping and receiving portions toward and away from each other while maintaining the alignment between the guide wire and catheter for fitting the guide wire in the catheter upon relative shifting of the gripping and receiving portions toward each other and for allowing the receiving portion to be used to apply a turning force to the held guide wire, wherein the gripping portion comprises at least one guide wire grasping member and a biasing mechanism that provides a bias force to urge the grasping member into engagement with the guide wire for securely holding the guide wire, and the receiving portion has at least one surface arranged and configured to engage and shift the grasping member away from the guide wire against the bias force applied by the biasing mechanism during the relative shifting of the gripping and receiving portions toward each other.

7. The tool of claim 6 wherein the grasping member and receiving portion surface include restraining structure therebetween which restrains the engaged and shifted grasping member against shifting back toward the guide wire when the relative shifting between the gripping and receiving portions ceases.

* * * * *